(12) United States Patent
Engsberg et al.

(10) Patent No.: US 6,913,586 B2
(45) Date of Patent: Jul. 5, 2005

(54) METHOD AND APPARATUS FOR DETERMINING A DORSIFLEXION ANGLE

(75) Inventors: Jack Engsberg, Eureka, MO (US); Kelly Jean King-Ellison, Minneapolis, MN (US); Nathaniel E. Hawkins, Lake Hiawatha, NJ (US)

(73) Assignee: Barnes-Jewish Hospital, St. Louis, MO (US)

( * ) Notice: Subject to any disclaimer, the term of this patent is extended or adjusted under 35 U.S.C. 154(b) by 20 days.

(21) Appl. No.: 10/685,010

(22) Filed: Oct. 14, 2003

(65) Prior Publication Data

US 2005/0080370 A1 Apr. 14, 2005

(51) Int. Cl.⁷ .......................... A61F 5/00; A61F 13/06; A41D 13/00
(52) U.S. Cl. .......................... 602/23; 602/27; 602/28; 602/29; 2/22; 128/892
(58) Field of Search .......................... 602/27, 28, 29, 602/65, 32, 16, 5, 6, 23; 2/24, 62, 22; 128/892

(56) References Cited

U.S. PATENT DOCUMENTS

| | | | | |
|---|---|---|---|---|
| 1,607,834 A | * | 11/1926 | Line .......................... | 602/15 |
| 2,099,401 A | * | 11/1937 | Jungmann .................... | 602/30 |
| 2,267,924 A | * | 12/1941 | Johnston ...................... | 602/39 |
| 2,428,342 A | * | 9/1947 | Sherman ...................... | 36/161 |
| 3,643,659 A | * | 2/1972 | Storer ......................... | 128/893 |
| 3,779,654 A | * | 12/1973 | Horne ......................... | 403/62 |
| 3,880,417 A | * | 4/1975 | Burris et al. ................. | 5/624 |
| 4,323,080 A | * | 4/1982 | Melhart ...................... | 600/587 |
| 4,572,170 A | * | 2/1986 | Cronk et al. ................. | 602/26 |
| 5,014,690 A | * | 5/1991 | Hepburn et al. .............. | 602/16 |
| 5,052,375 A | | 10/1991 | Stark et al. | |
| 5,176,623 A | * | 1/1993 | Stetman et al. .............. | 602/27 |
| 5,257,969 A | | 11/1993 | Mance | |
| 5,297,540 A | * | 3/1994 | Kaiser et al. ................. | 601/27 |
| 5,358,469 A | * | 10/1994 | Patchel et al. ................ | 602/5 |
| 5,358,471 A | | 10/1994 | Klotz | |
| 5,368,546 A | | 11/1994 | Stark et al. | |
| 5,429,588 A | | 7/1995 | Young et al. | |
| 5,484,389 A | | 1/1996 | Stark et al. | |
| 5,518,476 A | | 5/1996 | McLeon | |
| 5,540,706 A | | 7/1996 | Aust et al. | |
| 5,547,464 A | | 8/1996 | Luttrell et al. | |
| 5,571,078 A | * | 11/1996 | Malewicz ..................... | 602/27 |

(Continued)

OTHER PUBLICATIONS

Banks, H.H., and W.T. Green, 1958. The Correction of Equinus Deformity in Cerebral Palsy. *The Journal of Bone and Joint Surgery*, 40–A: 1359–1379.

(Continued)

*Primary Examiner*—Henry Bennett
*Assistant Examiner*—D. Doster-Greene
(74) *Attorney, Agent, or Firm*—Sonnenschein Nath & Rosenthal LLP

(57) ABSTRACT

Apparatus for determining a dorsiflexion angle of a surgical patient's foot relative to the corresponding leg during tendon surgery. The apparatus includes a leg member having a first support adapted for engaging at least one of a lateral malleolus and a medial malleolus of the patient, and a second support opposing the first support adapted for engaging another of the lateral malleolus and the medial malleolus of the patient. The apparatus further includes a foot member rotatably connected to the leg member for selectively rotating the foot member relative to the leg member about an axis defined by the first support and the second support of the leg member. The foot member has a metatarsal support adapted for engaging a predetermined point on at least one preselected metatarsal bone of the patient.

30 Claims, 8 Drawing Sheets

U.S. PATENT DOCUMENTS

| | | | |
|---|---|---|---|
| 5,613,976 | A | 3/1997 | Agee et al. |
| 5,797,918 | A | 8/1998 | McGuire et al. |
| 5,799,659 | A | 9/1998 | Stano |
| 5,847,464 | A | 12/1998 | Singh et al. |
| 5,921,009 | A | 7/1999 | Hice |
| 5,929,782 | A | 7/1999 | Stark et al. |
| 5,980,473 | A | 11/1999 | Korakianitis et al. |
| 6,024,474 | A | 2/2000 | Tanaka |
| 6,077,270 | A | 6/2000 | Katz |
| 6,184,797 | B1 | 2/2001 | Stark et al. |
| 6,206,807 | B1 | 3/2001 | Cowans et al. |
| 6,349,487 | B1 | 2/2002 | Hice |
| 6,368,353 | B1 | 4/2002 | Arcand |
| 6,515,593 | B1 | 2/2003 | Stark et al. |
| 6,607,202 | B1 | 8/2003 | Palmer |

OTHER PUBLICATIONS

Javors, J.R., and Klaaren, H.E., 1987. The Vulpius Procedure for Correction of Equinus Deformity in Cerebral Palsy. *Journal of Pediatric Orthopedics*, 7:191–193.

Gage, J.R., 1991. Gait Analysis in Cerebral Palsy. *Clinics in Developmental Medicine*, 121: 1–127.

Martz, C.D., 1960. Talipes Equinus Correction in Cerebral Palsy. *The Journal of Bone and Joint Surgery*, 42–A: 769–776.

Pierrot, A.H., and O.B. Murphy, 1974. Heel Cord Advancement: A New Approach to the Spastic Equinus Deformity. *Orthopedic Clinics of North America*, 5:117–124.

Strecker, W.B., M.W. Via, S.K. Oliver, and P.L. Schoenecker, 1990. Heel Cord Advancement for Treatment of Equinus Deformity in Cerebral Palsy. *Journal of Pediatric Orthopaedics*, 10:105–108.

Thometz, J., S. Simon, and R. Rosenthal, 1989. The Effect on Gait of Lengthening of the Medial Hamstrings in Cerebral Palsy. *The Journal of Bone and Joint Surgery, Incorporated*, 71–A:345–353.

Walker, J.L., DB. Stevens, N.S. Clark, and A.R. Opfell, 1994. Heel Cord Advancement in Children with Spastic Equinus Deformity. *Foot and Ankle International*, 15:536–540.

White, J.W., 1943. Progress in Orthopedic Surgery. *Archives of Surgery*, 47:483–491.

White, J.W., 1943. Torsion of the Achilles Tendon: Its Surgical Significance. *Archives of Surgery*, 46:784–787.

\* cited by examiner

METHOD AND APPARATUS FOR DETERMINING A DORSIFLEXION ANGLE

BACKGROUND OF THE INVENTION

The present invention relates generally to a dorsiflexion angle of a surgical patient's foot, and more specifically to a method and apparatus for determining a dorsiflexion angle of a surgical patient's foot during tendon surgery.

Cerebral palsy is a debilitating disease that affects many people. A common orthopedic problem in people with cerebral palsy is an equinus deformity, wherein the gastronemius and soleus muscles of the lower leg are permanently contracted. An equinus deformity may be surgically corrected if a tip-toe or toe-heel gait persists. Heel cord lengthening (HCL) surgery, in which the Achilles tendon is lengthened, is often used to correct equinus deformities. During the HCL surgery, a patient's foot is forcibly dorsiflexed (i.e., bending of the foot towards the shin) until the surgeon, based on his or her experience, subjectively determines the patient's foot is at a suitable maximum dorsiflexion angle with respect to the patient's corresponding leg. However, if the maximum dorsiflexion angle selected by the surgeon is too small, the patient's Achilles tendon will be under-stretched and the surgery may need to be repeated thereby increasing risk of complications to the patient. Additionally, if the maximum dorsiflexion angle selected by the surgeon is too high, the patient's Achilles tendon will be over stretched and the patient may have irreversible impaired function caused by an inability to produce adequate plantarflexion (i.e., bending of the foot away from the shin) torque during gait.

SUMMARY OF THE INVENTION

In one aspect, the present invention includes apparatus for determining a dorsiflexion angle of a surgical patient's foot relative to the corresponding leg during tendon surgery. The apparatus includes a leg member having a first support adapted for engaging at least one of a lateral malleolus and a medial malleolus of the patient, and a second support opposing the first support adapted for engaging another of the lateral malleolus and the medial malleolus of the patient. The apparatus further includes a foot member rotatably connected to the leg member for selectively rotating the foot member relative to the leg member about an axis defined by the first support and the second support of the leg member. The foot member has a metatarsal support adapted for engaging a predetermined point on at least one preselected metatarsal bone of the patient.

In another aspect, a method is provided for determining an angle of dorsiflexion of a surgical patient's foot during tendon surgery. The method includes establishing a first plane corresponding to the patient's leg by locating a lateral malleolus of the patient, locating a medial malleolus of the patient, and locating a predetermined point on the patient's leg above the lateral malleolus and the medial malleolus. The method further includes establishing a second plane corresponding to the patient's foot by locating a first metatarsal head of the patient and locating a second metatarsal head of the patient, and measuring an angle between the first plane and the second plane to determine the dorsiflexion angle of the patient's foot.

In yet another aspect, the present invention includes apparatus for determining a dorsiflexion angle of a surgical patient's foot relative to the corresponding leg during tendon surgery. The apparatus includes a leg member having a first support adapted for engaging at least one of a lateral malleolus and a medial malleolus of the patient, a second support opposing the first support adapted for engaging another of the lateral malleolus and the medial malleolus of the patient, and a reference arm extending from at least one of the first support and the second support adapted for engaging the leg of the patient at a predetermined point above the lateral malleolus and the medial malleolus of the patient. The apparatus further includes a foot member rotatably connected to the leg member for selectively rotating the foot member relative to the leg member about an axis defined by the first support and the second support of the leg member. The foot member has a metatarsal support adapted for engaging a predetermined point on at least one preselected metatarsal bone of the patient.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figures 1, 2:
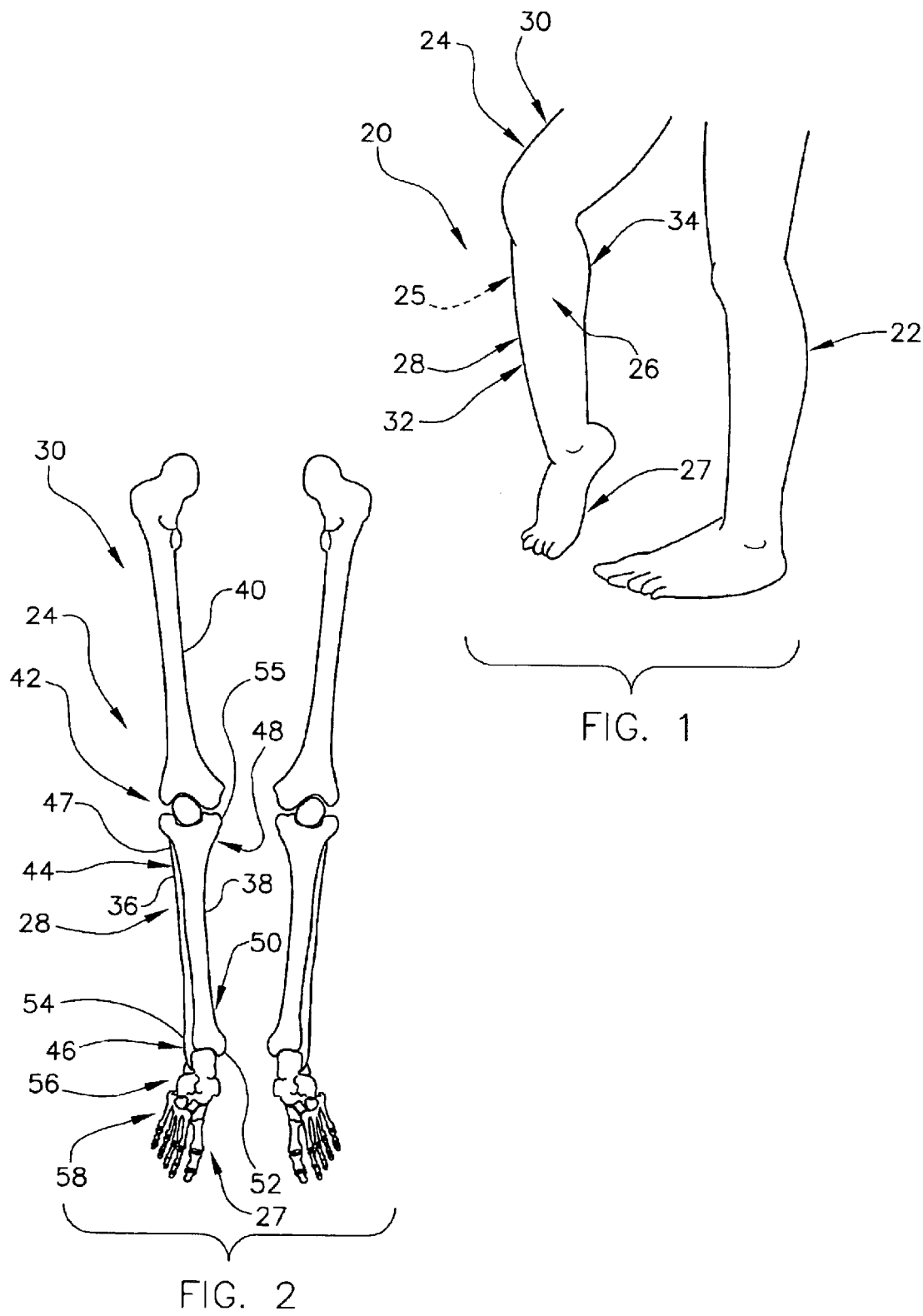
FIG. 1 is a perspective of a surgical patient's lower body having an equinus deformity in a right leg thereof.
FIG. 2 is a front elevation of a skeletal structure of the surgical patient's lower body shown in FIG. 1.

Referring now to the drawings, and more specifically to FIG. 1, a surgical patient's lower body is designated in its entirety by the reference numeral 20. The lower body 20 includes a left leg (generally designated by 22) and a right leg (generally designated by 24). The right leg 24 includes a lateral (i.e. outer) side (generally designated by 25), a medial (i.e. inner) side (generally designated by 26), a foot (generally designated by 27), a lower portion (generally designated by 28), and an upper portion (generally designated by 30). The lower portion 28 of the right leg 24 includes a shin (generally designated by 32) and a calf (generally designated by 34). The left leg 22 represents a leg having normal function, while the right leg 24 represents a leg having an equinus deformity. More specifically, the gastronemius and soleus muscles (not shown) of the calf 34 of the right leg 24 are permanently contracted. Tendon surgery (e.g., Heel cord lengthening (HCL) surgery) may be performed on the patient's right leg 24 to correct the equinus deformity by lengthening the Achilles tendon (not shown) attached to the gastronemius and soleus muscles.

Figure 3:
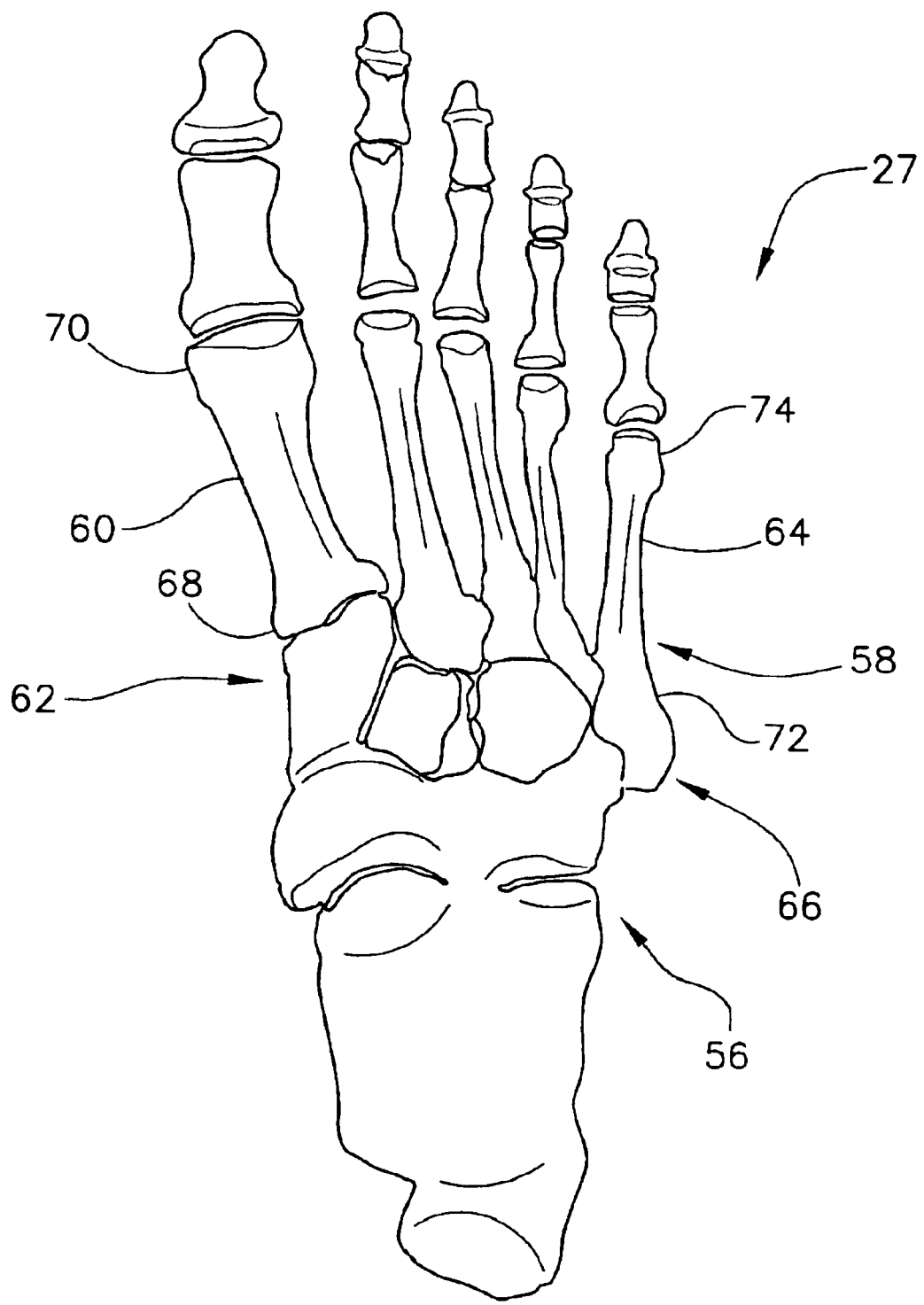
FIG. 3 is a top plan of the skeletal structure of a foot of the surgical patient.

As illustrated in FIG. 2, the lower portion 28 of the patient's right leg 24 includes a fibula 36 and a tibia 38, and the upper portion 30 of the patient's right leg includes a femur 40. A knee joint (generally designated by 42) joins the femur 40 to the fibula 36 and the tibia 38. The fibula 36 extends between the knee joint 42 and the foot 27, and includes an upper end (generally designated by 44) adjacent the knee joint and a lower end (generally designated by 46) opposite the upper end and adjacent the foot. The upper end 44 of the fibula 36 includes a head 47. The tibia 38 extends between the knee joint 42 and the foot 27, and includes an upper end (generally designated by 48) adjacent the knee joint 42 and a lower end (generally designated by 50) opposite the upper end and adjacent the foot. The lower end 50 of the tibia 38 includes a medial malleolus 52 (i.e., inner ankle bone protuberance) protruding therefrom and the lower end 46 of the fibula 36 includes a lateral malleolus 54 (i.e., outer ankle bone protuberance) protruding therefrom opposite the medial malleolus. The upper end 48 of the tibia 38 includes a medial condyle 55. The foot 27 includes a plurality of tarsal bones (generally designated by 56) extending from the respective lower ends 46, 50 of the fibula 36 and the tibia 38. A plurality of metatarsal bones (generally designated by 58) extend outwardly from the tarsal bones 56 to form the broad, long structure of the foot 27. More specifically, as illustrated in FIG. 3 the foot 27 includes five metatarsal bones 58, including a first metatarsal bone 60 on a medial side (generally designated by 62) of the foot and a fifth metatarsal bone 64 on a lateral side (generally designated by 66) of the foot. Each metatarsal bone 58 extends outward from a base adjacent the tarsal bones 56 to a head opposite the base. More specifically, the first metatarsal bone 60 (corresponding to the knuckle of the great toe) extends outwardly from a base 68 adjacent the tarsal bones 56 to a head 70 opposite the base 68, and the fifth metatarsal bone 64 extends outwardly from a base 72 adjacent the tarsal bones 56 to a head 74 opposite the base 68. Any of the metatarsal bones 58 may be referred to herein as a first and/or a second metatarsal bone. Additionally, any of the heads of the metatarsal bones 58 may be referred to herein as a first and/or a second metatarsal head.

Figure 4:
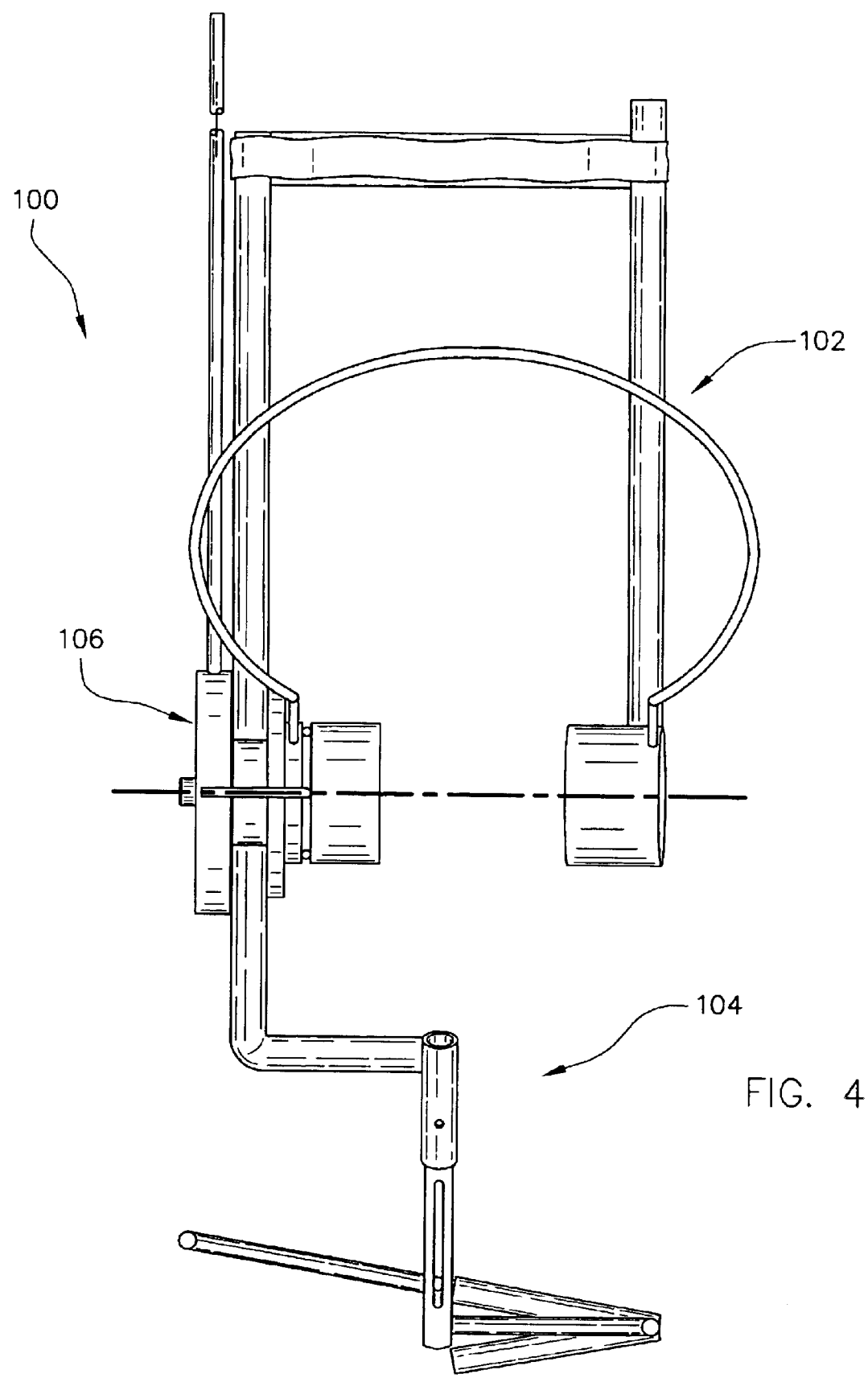
FIG. 4 is a perspective of apparatus of the present invention for determining a dorsiflexion angle of the surgical patient's foot relative to the patient's corresponding leg.
Figure 5:
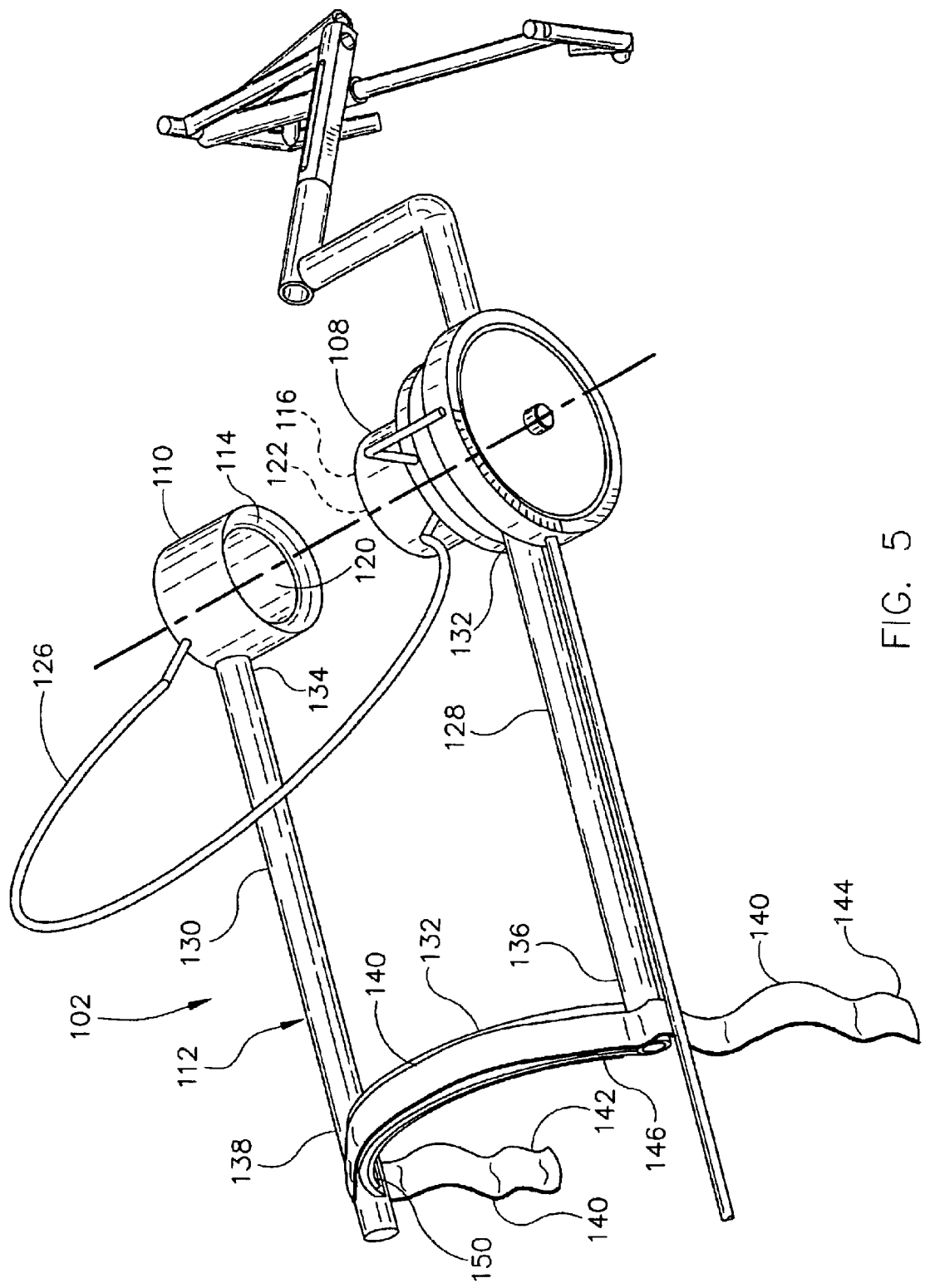
FIG. 5 is a perspective of a leg member of the apparatus illustrated in FIG. 4.

As illustrated in FIG. 4, apparatus of the present invention is designated in its entirety by the reference numeral 100. The apparatus 100 includes a leg member (generally designated by 102), a foot member (generally designated by 104) rotatably connected to the leg member for rotation relative to the leg member, and a gage (generally designated by 106) operatively connected between the leg member and the foot member for measuring an angle between the leg member and the foot member. As illustrated in FIG. 5, the leg member 102 includes a first support 108 and a second support 110 connected to and opposing the first support. In one embodiment, the leg member 102 includes a shin support (generally designated by 112) connecting the first support to the second support. In one embodiment, the first support 108 is adapted for engaging the patient's lateral malleolus 54 (FIG. 2), and the second support 110 is adapted for engaging the patient's medial malleolus 52 (FIG. 2). More specifically, in this embodiment the second support 110 includes a recess 114 sized and shaped to receive a portion of the patient's medial malleolus 52 therein. Similarly, the first support 108 includes a recess 116 sized and shaped to receive a portion of the patient's lateral malleolus 54 therein. In alternative embodiment, the first support 108 is adapted to engage the patient's medial malleolus 52, and the second support 110 is adapted for engaging the patient's lateral malleolus 54.

In one embodiment, the first and second supports 108, 110 each include a cushion (not shown) for engaging the patient's respective malleoli 54, 52 when they are received within the respective recesses 116, 114. More specifically, a cushion is positioned between each of the first and second supports 108, 110 and the patient's respective malleolus 54, 52 when the supports are engaged with the malleoli. In one embodiment, the cushions provide an appropriate coefficient of friction between an inner surface (not shown) of each of the cushions and skin tissue covering the patient's malleoli 52, 54 to securely engage the leg member 102, and more specifically the first and supports 108, 110, with the patient's malleoli. The cushions facilitate maintaining accurate location of the inner and first supports 110, 108 with respect to the patient's malleoli 52, 54 by providing an appropriate coefficient of friction as described above. Additionally, the cushions may improve the comfort of the apparatus 100 by cushioning the engagement between the first and second supports 108, 110 and the patient's respective malleoli 54, 52. Although other materials may be used without departing from the scope of the present invention, in one embodiment the cushions are formed from cotton batting. Additionally, although other materials may be used to provide the appropriate coefficient of friction (e.g., neoprene and/or a temporary adhesive) without departing from the scope of the present invention, in one embodiment the inner surface of one or more of the cushions is formed by attaching a layer of Dycem® to the cushions. Dycem is a federally registered trademark of Dycem Limited Corporation of Bristol, England. In an alternative embodiment, the inner surface of one or more of the cushions is defined by the material forming a majority of the cushion (e.g., cotton batting), wherein such material provides the predetermined coefficient of friction. In yet another alternative embodiment, the cushions are formed completely from the material providing the appropriate coefficient of friction (e.g., Dycem®, neoprene, and/or a temporary adhesive). Furthermore, in one embodiment an outer surface (not shown) of one or more of the cushions (opposite the inner surface) includes an adhesive for securely attaching the cushion(s) to the first and second supports 108, 110.

In one embodiment, the leg member includes a spring 126 for biasing the second support 110 toward the first support 108 to facilitate secure attachment of the leg member 102 to the patient's leg 24, and more specifically to facilitate secure engagement of the first support 108 with the patient's lateral malleolus 54 and to facilitate secure engagement of the second support 110 with the patient's medial malleolus 52. Although the exemplary spring 126 is described and illustrated herein as biasing the first and second supports 108, 110 toward each other, it should be understood that any other suitable biasing mechanism(s) may be used in place of the spring to bias the outer and second supports toward each other.

The shin support 112 includes a pair of extensions 128, 130 extending from the first support 108 and the second support 110 respectively, and a shin band 132. Each extension 128, 130 extends outward from a respective lower end 132, 134 (extending from the corresponding support 108, 110) to a respective upper end 136, 138. The shin band 132 extends between and connects the extensions 128, 130 adjacent their upper ends 136, 138. The shin support 112 is sized and shaped for receiving a portion of the patient's lower leg 28 (FIGS. 1 and 2) to facilitate secure attachment the leg member 102 to the patient's leg 24. More specifically, the shin band 132 is sized and shaped for receiving a portion of the patient's shin 32 (FIG. 1) therein. When the patient's shin 32 is received within the shin band 132, the shin band and the upper ends 136, 138 of the respective extensions 128, 130 generally surround a portion of the patient's shin 32 for securing the shin support 112 to the patient's shin to facilitate secure attachment of the leg member 102 to the patient's leg 24. In one embodiment, the shin band 132 is adapted to bias the upper ends 136, 138 of the respective extensions 128, 130 toward each other to facilitate securing the shin support 112 to the patient's shin 32.

In one embodiment, the shin support 112 includes a strap 140 attached to the shin support for securing the shin support to the patient's shin 32. Although the shin strap 140 may have other configurations without departing from the scope of the present invention, in the embodiment illustrated in FIG. 5 the shin strap 140 is attached to the shin band 132 and is adapted to surround a portion of the patient's calf 36 (FIG. 1) to securely attach the shin support 112 to the patient's shin 32. It should be understood that the shin strap 140 may be attached to one or more of the extensions 128, 130 and the shin band 132, and may be attached thereto using any suitable attachment (e.g., adhesive). Additionally, the strap 140 may be secured around the patient's calf 36 in any suitable manner. For example, in the exemplary embodiment the strap 140 includes opposite ends 142, 144 adapted to connect together to secure the strap around the patient's calf 36. The ends 142, 144 may be adapted to connect using any suitable attachment (e.g., hook and loop fasteners). In another embodiment (not shown), the strap 140 is a continuous loop of elastic material adapted to receive a portion of the patient's lower leg 28 therein.

In one embodiment, the shin band 132 includes a cushion (generally designated by 146) for engaging the patient's shin 32 when it is received within the shin band. More specifically, the cushion 146 is positioned between the shin band 132 and the patient's shin 32 when the shin support 112 is securely attached to the patient's shin. In one embodiment, the cushion 146 provides an appropriate coefficient of friction between an inner surface 150 of the cushion and skin tissue of the patient's shin 32 to securely attach the shin support 112 to the patient's shin. The cushion 146 facilitates maintaining accurate location of the shin support 112 with respect to the patient's shin 32 by providing an appropriate coefficient of friction as described above. Additionally, the cushion 146 may improve the comfort of the apparatus 100 by cushioning the engagement between the shin support 112, and more specifically the shin band 132, and the patient's shin 32. Although other materials may be used without departing from the scope of the present invention, in one embodiment the cushion 146 is formed from cotton batting. Additionally, although other materials may be used to provide the appropriate coefficient of friction (e.g., neoprene and/or a temporary adhesive) without departing from the scope of the present invention, in one embodiment the inner surface 150 of the cushion 146 is formed by attaching a layer of Dycem® to the cushion 146. In an alternative embodiment, the inner surface 150 of the cushion 146 is defined by the material forming a majority of the cushion (e.g., cotton batting), wherein such material provides the appropriate coefficient of friction. In yet another alternative embodiment, the cushion 146 is formed completely from the material providing the appropriate coefficient of friction (e.g., Dycem®, neoprene, and/or a temporary adhesive).

In one embodiment, an outer surface (not shown) of the cushion 146 (opposite the inner surface 150) includes an adhesive for securely attaching the cushion 146 to the shin band 132. Additionally, in one embodiment the cushion 146 also extends between the upper ends 136, 138 of the respective extensions 128, 130 to facilitate secure attachment of the shin support 112 to the patient's shin 32 by providing an appropriate coefficient of friction as described above, and to cushion the engagement between the upper ends and the patient's shin 32.

Figure 6:
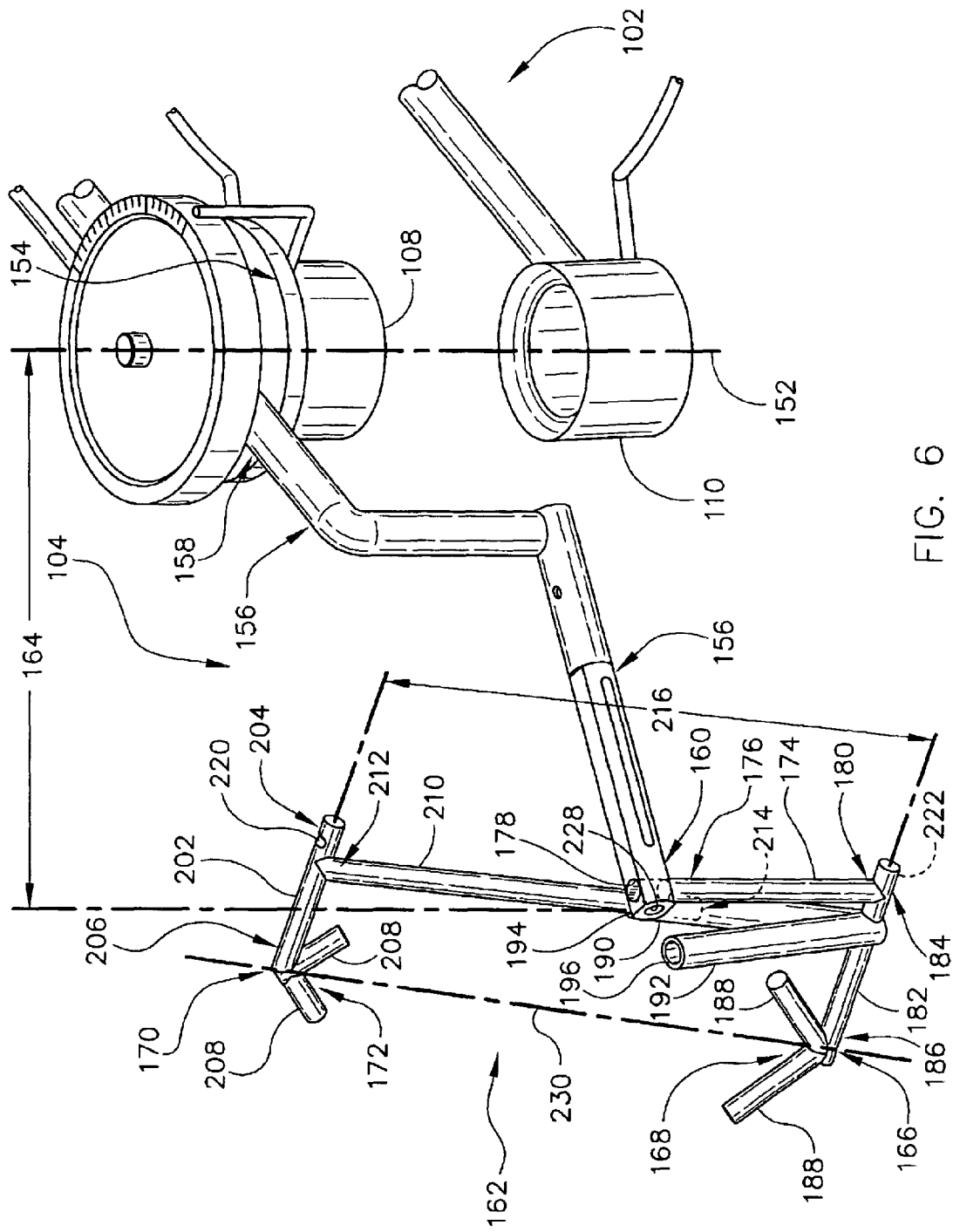
FIG. 6 is a perspective of a foot member of the apparatus adapted for engaging a patient's right foot.

As illustrated in FIG. 6 and described above, the foot member 104 is rotatably connected to the leg member 102 for rotation relative to the leg member. More specifically, the foot member 104 is rotatably connected to the leg member 102 for selective rotation of the foot member relative to the leg member about an axis 152 defined by the first and second supports 108, 110 of the leg member. Although other rotatable connections may be used without departing from the scope of the present invention, in one embodiment the foot member 104 and the leg member 102 are connected by a clevis joint (generally designated by 154) having an axis of rotation generally coincident with the axis 152 defined by the first and second supports 108, 110. It should be understood that any suitable rotatable connection (e.g., a conventional ball bearing joint, a conventional friction joint) may be used to rotatably connect the leg and foot members 102, 104, and accordingly the clevis joint 154 is meant as exemplary only. Additionally, although the leg member 102 and the foot member 104 are illustrated herein as being rotatably connected adjacent the first support 108, it should be understood that the leg member and the foot member may be rotatably connected adjacent the second support 110. In one embodiment a stop (not shown) is connected to one of the leg member 102 and the foot member 104 for limiting rotation of the foot member relative to the leg member.

The foot member 104 includes a rotating arm (generally designated by 156) extending outward from the joint 154 connecting the leg member 102 and the foot member 104. The arm 156 extends from a first end (generally designated by 158) extending from the joint 154 to a second end (generally designated by 160) opposite the first end. A metatarsal support (generally designated by 162) extends from the second end 160 of the arm 156 for engaging a predetermined point on at least one preselected metatarsal bone 58 (FIGS. 2 and 3) of the patient. The second end 160 of the rotating arm 156 is adapted to telescope outwardly away from the first end 158 for selective adjustment of a length 164 of the foot member 104, and more specifically the arm 156, to accommodate a range of different foot lengths. In one embodiment, the length 164 is selectively adjustable between about 2.5 centimeters and about 25 centimeters to accommodate foot lengths between about 4 centimeters and about 40 centimeters. In the embodiment illustrated in FIG. 6, the metatarsal support 162 includes a first metatarsal support (generally designated by 166) having a recess (generally designated by 168) for receiving the head 70 (FIG. 3) of the first metatarsal bone 60 (FIG. 3), and a fifth metatarsal support (generally designated by 170) having a recess (generally designated by 172) for receiving the head 74 (FIG. 3) of the fifth metatarsal bone 64 (FIG. 3). However, it should be understood that the metatarsal support 162 may receive and engage any or all of the metatarsal bones 58 of the patient. Additionally, although the metatarsal support 162 is described and illustrated herein as receiving and engaging the heads of the metatarsal bones 58, it should be understood that the metatarsal support 162 may be adapted to receive and engage any portion of one or more of the metatarsal bones. It is also envisioned within the scope of the present invention that the metatarsal support 162 may receive and engage other bones of the patient's foot 27 (FIGS. 1–3) in addition or in alternative to the metatarsal bones 58. Furthermore, either of the recesses 168, 172 may be referred to herein as a first and/or a second recess.

The first metatarsal support 166 includes a first arm 174 extending from the second end 160 of the rotating arm 156. The first arm 174 includes an inner end (generally designated by 176) removably received within an opening 178 in the second end 160 of the rotating arm 156, and an outer end (generally designated by 180) opposite the inner end. A second arm 182 extends from an upper end (generally designated by 184), extending from the first arm 174, to a lower end (generally designated by 186) opposite the upper end. A plurality of first metatarsal support members 188 extend from the lower end 186 of the second arm 182 to define the recess 168 of the first metatarsal support 166. Additionally, a plurality of female cross-members 190, 192 extend from the second arm 182 of the first metatarsal support 166 generally towards the fifth metatarsal support 170. Each of the female cross-members 190, 192 includes a generally cylindrical opening 194, 196, respectively. The fifth metatarsal support 170 includes a first arm 202 extending between an upper end (generally designated by 204) and a lower end (generally designated by 206). A plurality of fifth metatarsal support members 208 extend from the lower end 206 of the first arm 202 to define the recess 172 of the fifth metatarsal support 170.

Although the recess 168 of the first metatarsal support 166 is illustrated herein as being defined by two support members 188, and the recess 172 of the fifth metatarsal support 170 is illustrated herein as being defined by two support members 208, it should be understood that the recesses 168, 172 may have other configurations without departing from the scope of the present invention. Additionally, although the recesses 168, 172 are described and illustrated herein in the exemplary manner, it should be understood that the recesses may be formed from any suitable structure(s) such that the recesses are adapted to receive and support one or more of the metatarsal bones 58, and/or one or more of any other bones of the patient's foot 27.

A male cross-member 210 extends from an outer end (generally designated by 212), extending from the first arm 202, to an inner end (generally designated by 214) opposite the outer end. The male cross-member 210 is sized and shaped to be selectively received within each of the openings 194, 196 of the female cross-members 190, 192. Additionally, the male cross-member 210 is adapted to be slidably received within the openings 194, 196 of the female cross-members 190, 192 for selective adjustment of a width 216 of the foot member 104, and more specifically the metatarsal support 162, to accommodate a range of different foot widths. In one embodiment, the width 216 is selectively adjustable between about 2 centimeters and about 20 centimeters to accommodate foot widths between about 2 centimeters and about 20 centimeters. In one embodiment, the metatarsal support 162 includes a biasing mechanism 218 (FIG. 9) for biasing the fifth metatarsal support 170 toward the first metatarsal support 166 to facilitate secure attachment of the foot member 104 to the patient's foot 27, and more specifically to facilitate secure engagement of the first metatarsal support with the patient's first metatarsal bone 60 and to facilitate secure engagement of the fifth metatarsal support with the patient's fifth metatarsal bone 64. Although the biasing mechanisms may have other configurations without departing from the scope of the present invention, in the embodiment illustrated in FIG. 9 the biasing mechanism 218 is an elastic band received within a notch 220 (FIG. 6) in the upper end 184 of the second arm 182 of the first metatarsal support 166, and received within a notch 222 (FIG. 7) in the upper end 204 of the first arm 202 of the fifth metatarsal support 170. Alternatively, the metatarsal support 170 may not include any biasing mechanism 218 so the first and fifth metatarsal supports 166, 170 are not biased toward each other.

Although the apparatus 100 has hereto been described and illustrated with regard to the right leg 24 (FIGS. 1 and 2) and the right foot 27 (FIGS. 1–3) of a surgical patient having an equinus deformity in the right leg 24, the apparatus is also adapted to accommodate a patient (not shown) having an equinus deformity in a left leg (not shown). More specifically, and as is described in more detail below, the metatarsal support 162 is adapted to connect to the rotating arm 156 in the orientation shown in FIG. 6, wherein the metatarsal support accommodates the right foot 27, and the orientation shown in FIG. 7, wherein the metatarsal support accommodates a left foot (not shown) of the left leg having an equinus deformity.

As illustrated in FIG. 6, the foot member 104, and more specifically the metatarsal support 162, is orientated to accommodate the right foot 27 of the patient (FIG. 1). More specifically, the first arm 174 of the first metatarsal support 166 is received at its inner end 176 within the opening 178 in the second end 160 of the rotating arm 156, such that the arm 174 extends outward from the second end of the rotating arm towards the second support 110. In one embodiment the second end 160 of the rotating arm includes a threaded opening 228 extending generally perpendicular to, and intersecting, the opening 178 for threadably receiving a set screw (not shown). When the set screw is threadably received within the opening 228, an end (not shown) of the set screw engages the inner end 176 of the first arm 174 to securely connect the first arm to the rotating arm 156. The female cross-member 190 receives the male cross-member 210 such that its inner end 214 is received within the opening 194 of the female cross-member and the male cross-member extends outward from the female cross-member toward the first support 108 of the leg member 102. As illustrated in FIG. 6, the female cross-member 190 is obliquely aligned relative to the axis 152 defined by the first and second supports 108, 110 of the leg member 102 to generally align the recesses 168, 172 of the respective first and fifth metatarsal supports 166, 170 with the patient's respective metatarsal bones 60, 64. More specifically, when the metatarsal support 162 is orientated as described above and illustrated in FIG. 6, the recesses 168, 172 of the first and fifth metatarsal supports 166, 170 generally lie along a line 230 extending oblique to the axis 152. Accordingly, when the first and second supports 108, 110 of the leg member 102 are respectively engaged with the patient's lateral and medial malleoli 54, 52, the recess 168 of the first metatarsal support 166 is generally aligned to receive the head 70 of the first metatarsal bone 60, and the recess 172 of the fifth metatarsal support 170 is generally aligned to receive the head 74 of the fifth metatarsal bone 64. In one embodiment, the female cross-member 190 and the line 230 are obliquely aligned relative to the axis 152 by an angle of about 10°. However, it should be understood that the female cross-member 190 and the line 230 may be aligned relative to the axis 152 by any suitable angle to generally align the recesses 168, 172 with the patient's corresponding metatarsal bones 60, 64.

Figure 7:
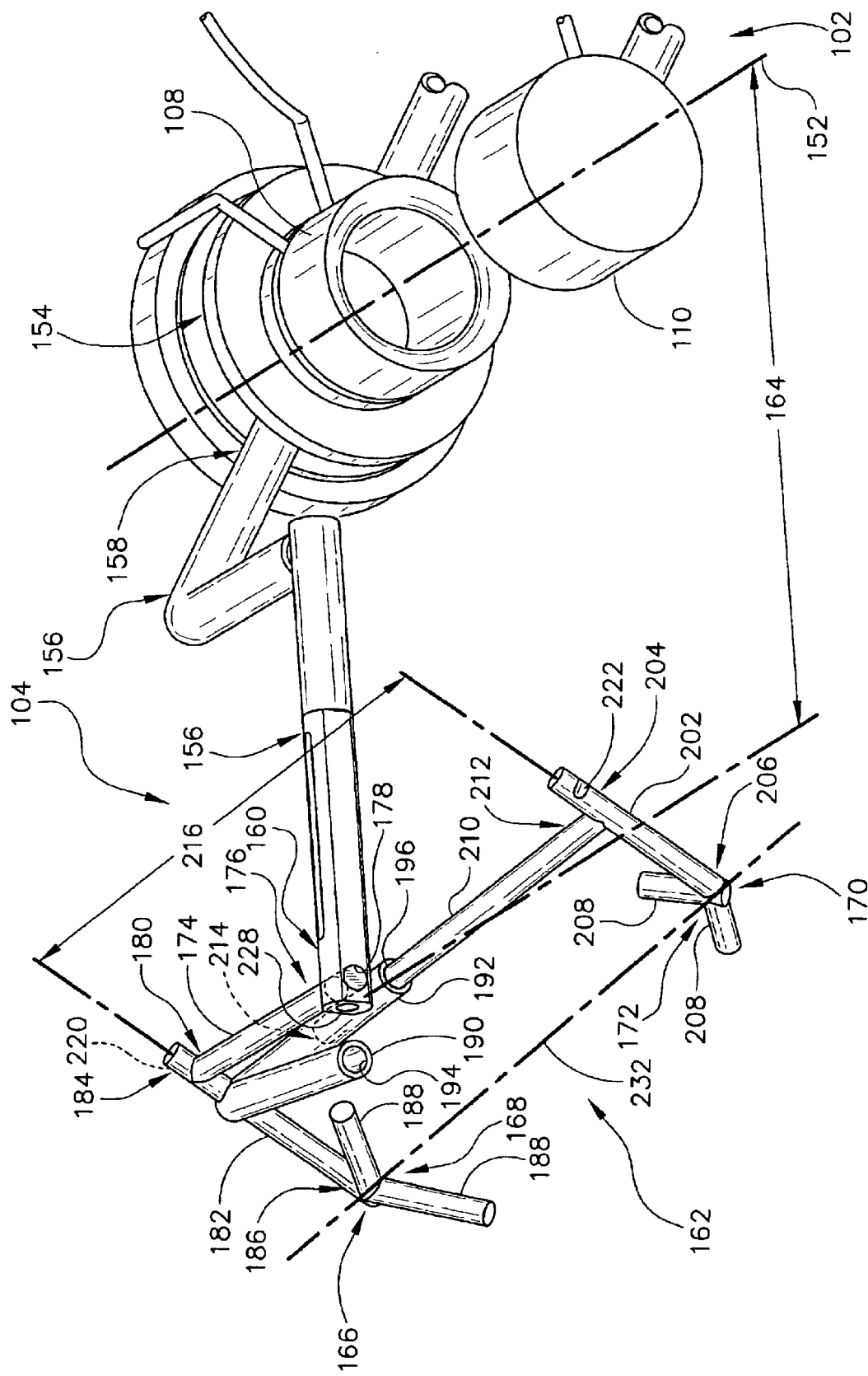
FIG. 7 is a perspective of a foot member of the apparatus adapted for engaging a patient's left foot.

As illustrated in FIG. 7, the foot member 104, and more specifically the metatarsal support 162, is orientated to accommodate a left foot of a surgical patient (not shown) having an equinus deformity in the patient's left leg (not shown). More specifically, the first arm 174 of the first metatarsal support 166 is received at its inner end 176 within the opening 178 in the second end 160 of the rotating arm 156, such that the arm 174 extends outward from the second end of the rotating arm towards the first support 108. The female cross-member 192 receives the male cross-member 210 such that its inner end 214 is received within the opening 196 of the female cross-member and the male cross-member extends outward from the female cross-member toward the second support 110 of the leg member 102. As illustrated in FIG. 7, the female cross-member 192 is obliquely aligned relative to the axis 152 defined by the first and second supports 108, 110 of the leg member 102 to generally align the recesses 168, 172 of the respective first and fifth metatarsal supports 166, 170 with the first and fifth metatarsal bones (not shown) of the patient's left foot. More specifically, when the metatarsal support 162 is orientated as described above and illustrated in FIG. 7, the recesses 168, 172 of the first and fifth metatarsal supports 166, 170 generally lie along a line 232 extending oblique to the axis 152. Accordingly, when the first and second supports 108, 110 of the leg member 102 are respectively engaged with a lateral malleolus (not shown) and a medial malleolus (not shown) of the patient's left leg, the recess 168 of the first metatarsal support 166 is generally aligned to receive a head (not shown) of the first metatarsal bone of the patient's left leg, and the recess 172 of the fifth metatarsal support 170 is generally aligned to receive a head (not shown) of the fifth metatarsal bone of the patient's left leg. In one embodiment, the female cross-member 192 and the line 232 are obliquely aligned relative to the axis 152 by an angle of about 10°. However, it should be understood that the female cross-member 192 and the line 232 may be aligned relative to the axis 152 by any suitable angle to generally align the recesses 168, 172 with the patient's corresponding metatarsal bones.

Although the metatarsal support 162 is herein described and illustrated as including two female cross-members 190, 192, it should be understood that the metatarsal support may include any number of female cross-members each having a unique alignment with the axis 152 to accommodate many different sizes and shapes of both left and right feet.

In one embodiment, each of the first and fifth metatarsal supports 166, 170 includes a cushion (not shown) for engaging the patient's first and fifth metatarsal bones 60, 64, respectively, when they are received within the respective recesses 168, 172 of the first and fifth metatarsal supports. More specifically, a cushion is positioned between each first and fifth metatarsal support 166, 170 and the patient's respective first and fifth metatarsal bones 60, 64 when the metatarsal bones are received within the respective recesses 168, 172 of the first and fifth metatarsal supports. In one embodiment, the cushions provide an appropriate coefficient of friction between an inner surface (not shown) of each cushion and skin tissue covering the patient's first and fifth metatarsal bones 60, 64 to securely engage the foot member 102, and more specifically the first and fifth metatarsal supports 166, 170, with the patient's first and fifth metatarsal bones, respectively. The cushions facilitate maintaining accurate location of the first and fifth metatarsal supports 166, 170 with respect to the patient's first and fifth metatarsal bones 60, 64 by providing an appropriate coefficient of friction as described above. Additionally, the cushions may improve the comfort of the apparatus 100 by cushioning the engagement between the first and fifth metatarsal supports 166, 170 and the patient's first and fifth metatarsal bones 60, 64. Although other materials may be used without departing from the scope of the present invention, in one embodiment the cushions are formed from cotton batting. Additionally, although other materials may be used to provide the appropriate coefficient of friction (e.g., neoprene and/or a temporary adhesive) without departing from the scope of the present invention, in one embodiment the inner surface of each cushion is formed by attaching a layer of Dycem® to the cushion. In an alternative embodiment, the inner surface of each cushion is defined by the material forming a majority of the cushion (e.g., cotton batting), wherein such material provides the appropriate coefficient of friction. In yet another alternative embodiment, the cushions are formed completely from the material providing the appropriate coefficient of friction (e.g., Dycem®, neoprene, and/or a temporary adhesive). Furthermore, in one embodiment an outer surface (not shown) of each cushion (opposite the inner surface) includes an adhesive for securely attaching the cushion(s) to the first and fifth metatarsal supports 166, 170.

Figure 8:
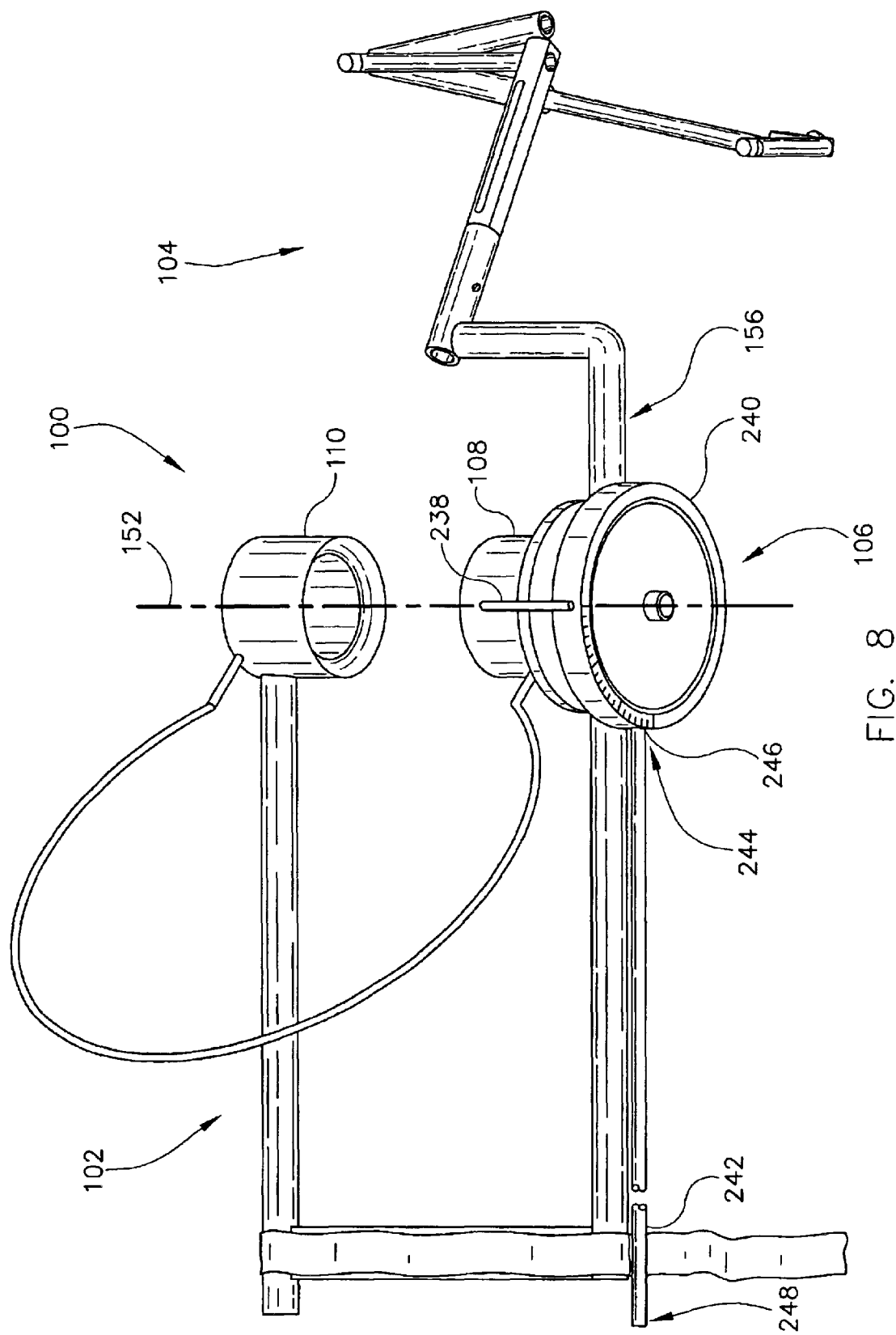
FIG. 8 is a perspective of the apparatus illustrating a gage of the present invention.

As illustrated in FIG. 8, the gage 106 is operatively connected between the leg member 102 and the foot member 104 for generally measuring an angle between the leg member and the foot member. The gage 106 includes an angle indicator 238, and a legend 240. The angle indicator 238 is connected to the foot member 104, and more specifically the rotating arm 156, for rotation with the foot member about the axis 152. The legend 240 is connected to the leg member 102 adjacent the first support 108 and the angle indicator 238 for generally indicating the angle between the leg member 102 and the foot member 104, as is described in more detail below. A reference arm 242 extends from a first end (generally designated by 244), received within an opening 246 in the legend 240, to a second end (generally designated by 248) adapted to engage the right leg 24 (FIGS. 1 and 2) of the surgical patient (FIG. 1) at a predetermined point above the lateral malleolus 54 (FIG. 2) and the medial malleolus 52 (FIG. 2) of the patient. In an alternative embodiment, the reference arm 242 extends from an opening (not shown) in the first support 108 of the leg member 102.

Figure 9:
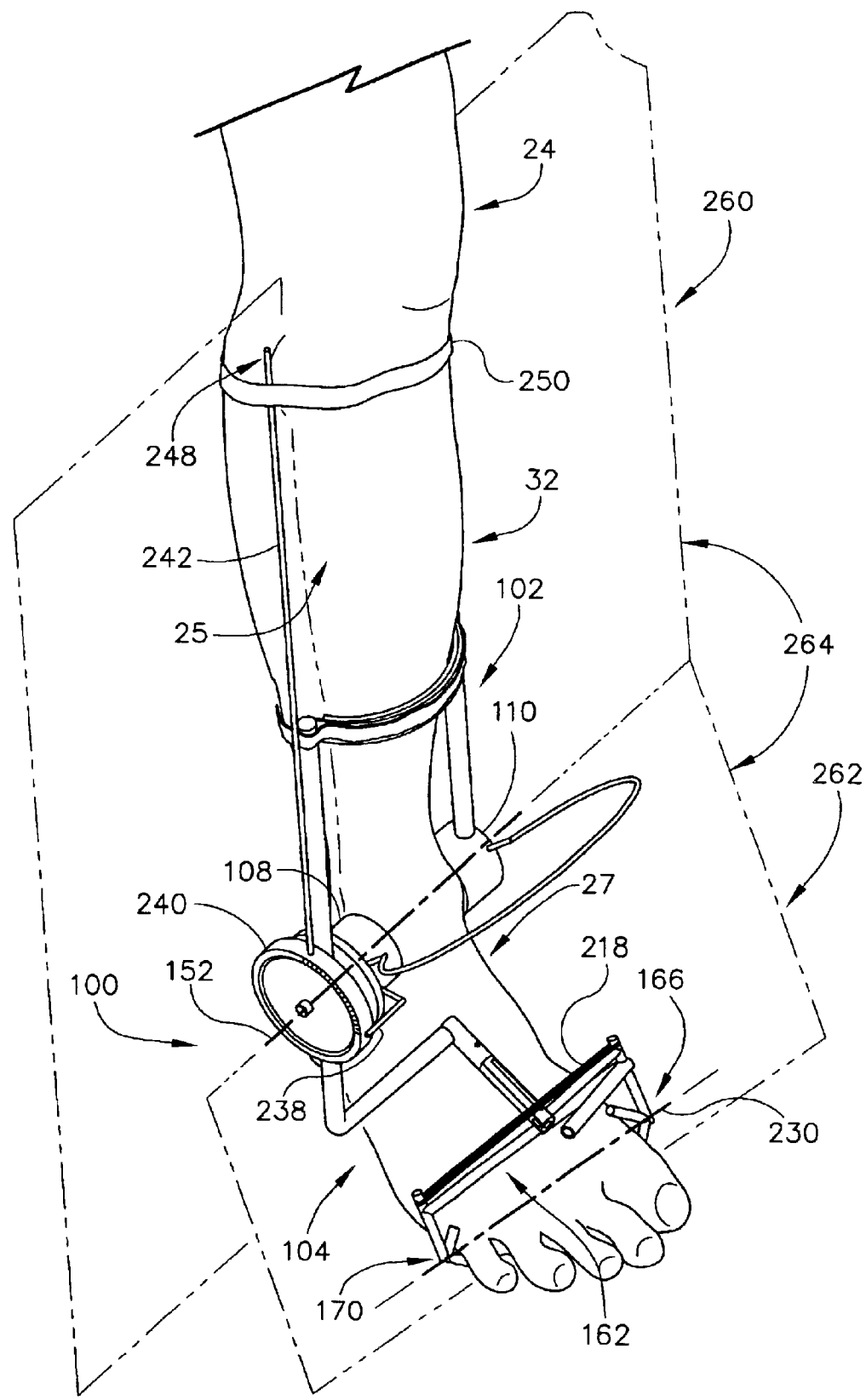
FIG. 9 is a perspective of the apparatus engaging a leg and a foot of the surgical patient shown in FIG. 1.

As illustrated in FIG. 9, the second end 248 of the reference arm 242 is adapted to engage a predetermined point above the medial and lateral malleoli 52, 54 (FIG. 2) on the lateral side 25 of the patient's right leg 24. For example, in one embodiment the second end 248 of the reference arm 242 is adapted to engage the head 47 (FIG. 2) of the fibula 36 (FIG. 2) of the patient's right leg 24. However, to accommodate left legs having an equinus deformity, the second end 248 of the reference arm 242 is also adapted to engage a predetermined point on a medial side (not shown) of a left leg (not shown) having an equinus deformity. For example, in one embodiment the second end 248 of the reference arm 242 is adapted to engage a medial condyle (not shown) of a tibia (not shown) of a left leg having an equinus deformity. It should be understood that the predetermined point on either a right leg or a left leg may include any suitable point above the medial and lateral malleoli of the corresponding leg, whether or not such point is explicitly referenced herein. Additionally, although the reference arm 242 and the gage 106 are described and illustrated herein as being operatively connected between the leg member 102 and the foot member 104 adjacent the first support 108, it should be understood that the reference arm and the gage may be operatively connected between the leg member and the foot member adjacent the second support 110. In such an alternative embodiment, the reference arm 242 may extend from the gage 106 or may extend from the second support 110, and the reference arm is adapted to engage a predetermined point (e.g., a head of a fibula) on a lateral side (not shown) of a left leg having an equinus deformity, and is adapted to engage a predetermined point (e.g., the medial condyle 55 (FIG. 2) of the tibia 38 (FIG. 2)) on the medial side 26 (FIG. 1) of the right leg 24. Additionally, in one embodiment the apparatus 100 includes a gage 106 and a reference arm 242 operatively connected between the leg member 102 and the foot member 104 adjacent the first support 108, and a gage 106 and a reference arm 242 operatively connected between the leg member and the foot member adjacent the second support 110.

In one embodiment, the reference arm 242 includes a strap 250 attached thereto for securely engaging the reference arm to the predetermined point on the leg 24 above the medial and lateral malleoli 52, 54. Although the strap 250 may have other configurations without departing from the scope of the present invention, in one embodiment, as shown in FIG. 9, the strap 250 is adapted to surround a portion of the patient's leg 24 to secure the reference arm 242 to the predetermined point. It should be understood that the strap 250 may be attached to the reference arm 242 using any suitable attachment (e.g., adhesive). Additionally, the strap 250 may be secured around the patient's leg in any suitable manner. For example, in the exemplary embodiment the strap 250 includes opposite ends (not shown) adapted to connect together to secure the strap around the patient's leg. The ends may be adapted to connect using any suitable attachment (e.g., hook and loop fasteners). In another embodiment (not shown), the strap 250 is a continuous loop of elastic material adapted to receive a portion of the patient's leg therein.

In one embodiment, the reference arm 242 includes a cushion (not shown) for engaging the patient's leg 24 (FIGS. 1 and 2) when the reference arm is engaged therewith. More specifically, the cushion is positioned between the reference arm 242 and the patient's leg 24 when the reference arm is engaged therewith. In one embodiment the cushion provides an appropriate coefficient of friction between an inner surface (not shown) of the cushion and skin tissue of the patient's leg 24 to securely engage the reference arm 242 to the patient's leg. The cushion facilitates maintaining accurate location of the reference arm 242 with respect to the predetermined point on the patient's leg 24 above the medial and lateral malleoli 52, 54 by providing an appropriate coefficient of friction as described above. Additionally, the cushion may improve the comfort of the apparatus 100 by cushioning the engagement between the reference arm 242 and the patient's leg 24. Although other materials may be used without departing from the scope of the present invention, in one embodiment the cushion is formed from cotton batting. Additionally, although other materials may be used to provide the appropriate coefficient of friction (e.g., neoprene and/or a temporary adhesive) without departing from the scope of the present invention, in one embodiment the inner surface of the cushion is formed by attaching a layer of Dycem® to the cushion. In an alternative embodiment, the inner surface of the cushion is defined by the material forming a majority of the cushion (e.g., cotton batting), wherein such material provides the appropriate coefficient of friction. In yet another alternative embodiment, the cushion is formed completely from the material providing the appropriate coefficient of friction (e.g., Dycem®, neoprene, and/or a temporary adhesive). In one embodiment, an outer surface (not shown) of the cushion (opposite the inner surface) includes an adhesive for securely attaching the cushion to the reference arm 242.

As illustrated in FIG. 9, the right leg 24 having an equinus deformity is received within the apparatus 100 to locate the patient's medial and lateral malleoli 52, 54 (FIG. 2), the patient's first and fifth metatarsals 60, 64 (FIG. 3), and the predetermined point on the leg above the medial and lateral malleoli. When located, the first and second supports 108, 110 engage the patient's respective lateral and medial malleoli 54, 52, the metatarsal support 162, and more specifically the respective first and fifth metatarsal supports 166, 170, engages the patient's first and fifth metatarsals 60, 64, and the reference arm 242 engages the predetermined point on the leg 24 above the medial and lateral malleoli.

In one embodiment, at least a portion of the legend 240 rotates relative to the corresponding support (e.g., the first support 108) such that a particular angle marking (e.g., 0°) on the legend can be positioned at a location corresponding to the location of the reference arm 242 on the apparatus 100. In such an embodiment wherein at least a portion of the legend 240 rotates relative to the first support 108, once the particular angle marking is positioned at the location corresponding to the reference arm 242, the particular angle marking can be fixed at such location in any suitable manner (e.g., a set screw) and the reference arm 242 may be removed from the apparatus 100. In an alternative embodiment, the entirety of the legend 240 is fixed relative to the corresponding support (e.g., the first support 108) such that the particular angle marking (e.g., 0°) positioned at the location corresponding to the reference arm 242 cannot be changed by rotating the legend, or a portion thereof, relative to the corresponding support.

By locating and engaging the medial and lateral malleoli 52, 54 and the predetermined point on the leg 24 above the medial and lateral malleoli, a first reference plane 260 is established corresponding to the leg 24. By locating and engaging the first and fifth metatarsals 60, 64 and the medial and lateral malleoli 52, 54, a second reference plane 262 is established corresponding to the patient's foot 27. An angle 264 measured between the first reference plane 260 and the second reference plane 262 corresponds to the angle between the leg member 102 and the foot member 104, and represents the dorsiflexion angle of the patient's foot 27. As the patient's foot 27 is dorsiflexed (i.e. bent upwards toward the shin 32) during surgery, the foot member 104 and the angle indicator 238 rotate along with the foot toward the leg member 102. The dorsiflexion angle 264 can then be determined from the gage 106 using the position of the angle indicator 238 relative to the legend 240. Additionally, as the patient's foot 27 is dorsiflexed the length 164 (FIGS. 6 and 7) of the rotating arm 156 (FIGS. 6 and 7) will automatically adjust to facilitate maintaining the location and engagement of the first and second supports 108, 110 relative to the patient's lateral and medial malleoli 54, 52 and the first and fifth metatarsal supports relative to the patient's first and fifth metatarsals 60, 64.

In one embodiment, the apparatus 100 is used during tendon surgery to record a maximum dorsiflexion angle 264 set during surgery, and the recorded dorsiflexion angle is used along with post-operative analysis of the results of the surgery to determine a desired maximum dorsiflexion angle for correcting an equinus deformity. In another embodiment, the apparatus 100 is used during tendon surgery to set a desired maximum dorsiflexion angle 264 for the particular surgical patient.

In one embodiment, the cushions of the first and second supports 108, 110, the cushion 146 (FIG. 5), the cushions of the first and fifth metatarsal supports 166, 170, and the cushion of the reference arm 242 facilitate maintaining accurate location of the first and second supports 108, 110, the shin support 112, the first and fifth metatarsal supports 166, 170, and the reference arm 242 by providing an appropriate coefficient of friction as described above.

Accordingly, in such an embodiment, the cushions facilitate accurate measurement of the dorsiflexion angle 264.

In an alternative embodiment, the legend 240 is connected to the foot member 104 for rotation with the foot member about the axis 152 and the gage 106 does not include the angle indicator 238. Rather, in such an alternative embodiment wherein the legend 240 is connected to the foot member 104 for rotation with the foot member, the dorsiflexion angle 264 can be determined from the gage 106 using the position of the legend relative to the reference arm 242. Additionally, in another alternative embodiment, the apparatus 100 does not include the gage 106 and the dorsiflexion angle 264 is read using a gage (not shown) separate from the apparatus by measuring the angle between a predetermined point on the reference arm 242 (and/or the patient's leg 24) and a predetermined point on the foot member 104 (and/or the patient's foot 27).

Although the apparatus 100 is described and illustrated herein as adjustable to accommodate varying foot lengths and widths, it should be understood that the apparatus in its entirety may also be suitably sized and/or shaped to accommodate a particular size and/or shape, or a particular range of sizes and/or shapes, of a patient's leg, including all its associated elements such as the foot and ankle. Accordingly, differently sized and/or shaped apparatus 100 may be used to accommodate different patients, depending on the sizes and/or shapes of the patients' legs. For example, an apparatus 100 accommodating a juvenile patient may be generally smaller and/or differently shaped than an apparatus accommodating an adult patient. Although the apparatus 100 is described herein with respect to tendon surgery, and for example with respect to HCL surgery, it should be understood that the apparatus is generally applicable to any surgery wherein determining a dorsiflexion angle of a patient's foot may be relevant. Accordingly, practice of the present invention is not limited to HCL surgery, correction of an equinus deformity, or tendon surgery generally.

The above-described apparatus is cost-effective and reliable for determining a dorsiflexion angle of a surgical patient's foot relative to the patient's corresponding leg during tendon surgery. More specifically, the apparatus may be used to record a maximum dorsiflexion angle set during surgery, and the recorded dorsiflexion angle may be used along with post-operative analysis of the results of the surgery to determine a desired maximum dorsiflexion angle for correcting an equinus deformity. Different desired maximum dorsiflexion angles can be determined using the apparatus to account for a variety of factors, including the age and development of the patient. Additionally, the apparatus can be used to set a desired maximum dorsiflexion angle for a particular surgical patient, such that the patient's Achilles tendon will not be under-stretched or overstretched during surgery. Accordingly, apparatus of the present invention facilitates accurate determination of a desired maximum dorsiflexion angle that may not result in impairment of function post-operatively or require another surgery, and facilitates setting such a desired maximum dorsiflexion angle during surgery.

Exemplary embodiments of apparatus for determining a dorsiflexion angle of a surgical patient's foot relative to the patient's corresponding leg during tendon surgery are described above in detail. The apparatus are not limited to the specific embodiments described herein, but rather, components of each apparatus may be utilized independently and separately from other components described herein. Each apparatus component can also be used in combination with other apparatus components.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for determining a dorsiflexion angle of a surgical patient's foot relative to the corresponding leg during tendon surgery, said apparatus comprising:
a leg member having a first support adapted for engaging the patent's leg adjacent at least one of a lateral malleolus and a medial malleolus of the patient, and a second support opposing the first support adapted for engaging the patent's leg adjacent another of the lateral malleolus and the medial malleolus of the patient; and
a foot member rotatably connected to the leg member for selectively rotating the foot member relative to the leg member about an axis defined by the first support and the second support of the leg member, the foot member having a metatarsal support adapted for engaging the patent's leg adjacent a predetermined point on at least one preselected metatarsal bone of the patient.

2. Apparatus in accordance with claim 1 further comprising a gage operatively connected between the leg member and the foot member for measuring an angle between the leg member and the foot member.

3. Apparatus in accordance with claim 2 wherein the gage comprises an angle indicator connected to one of the leg member and the foot member for rotation with the respective member about the axis and a legend connected to another of the leg member and the foot member adjacent the angle indicator for indicating the angle between the leg member and the foot member, said angle being representative of the dorsiflexion angle of the surgical patient's foot.

4. Apparatus in accordance with claim 2 further comprising a reference arm extending from the gage adapted for engaging the leg of the patient at a predetermined point above the lateral malleolus and the medial malleolus of the patient.

5. Apparatus in accordance with claim 4 wherein the reference arm comprises a first end adapted to be received within an opening in the gage, and a second end adapted for engaging the patent's leg adjacent a head of a fibula of the patient's leg.

6. Apparatus in accordance with claim 4 wherein the reference arm comprises a first end adapted to be received within an opening in the gage, and a second end adapted for engaging the patent's leg adjacent a medial condyle of a tibia of the patient's leg.

7. Apparatus in accordance with claim 4 wherein the reference arm further comprises a strap attached to the reference arm for securing the reference arm to the predetermined point above the lateral malleolus and the medial malleolus of the patient.

8. Apparatus in accordance with claim 1 wherein the leg member and the foot member are connected by a clevis joint having an axis of rotation generally coincident with said axis defined by the first support and the second support of the leg member.

9. Apparatus in accordance with claim 1 wherein the leg member further comprises a shin support connecting the first support to the second support and being sized and shaped for receiving a portion of the patient's shin.

10. Apparatus in accordance with claim 9 wherein the shin support includes a cushion for engaging the patient's shin when the patient's shin is received within the shin support.

11. Apparatus in accordance with claim 8 wherein the leg member further comprises a strap attached to the shin support for securing the shin support to the patient's shin to facilitate secure attachment of the leg member to the patient's leg.

12. Apparatus in accordance with claim 1 further comprising a spring for biasing the second support toward the first support to facilitate secure attachment of the leg member to the patient's leg.

13. Apparatus in accordance with claim 1 wherein the metatarsal support has a recess for receiving one of a first metatarsal head and a fifth metatarsal head of the patient therein.

14. Apparatus in accordance with claim 1 wherein the metatarsal support has a first recess for receiving a first metatarsal head of the patient's foot and a second recess opposing said first recess for receiving a fifth metatarsal head of the patient's foot.

15. Apparatus in accordance with claim 14 wherein the first and second recesses lie along a line extending obliquely with respect to the axis defined by the first support and the second support of the leg member.

16. Apparatus in accordance with claim 15 wherein the line extends obliquely at an angle of about 10° with respect to the axis defined by the first support and the second support of the leg member.

17. Apparatus in accordance with claim 1 further comprising a stop connected to one of the leg member and the foot member for limiting rotation of the foot member relative to the leg member.

18. A method for determining an angle of dorsiflexion of a surgical patient's foot during tendon surgery, said method comprising the steps of:
   establishing a first plane corresponding to the patient's leg by locating a lateral malleolus of the patient, locating a medial malleolus of the patient, and locating a predetermined point on the patient's leg above the lateral malleolus and the medial malleolus;
   establishing a second plane corresponding to the patient's foot by locating a first metatarsal head of the patient and locating a second metatarsal head of the patient; and
   measuring an angle between the first plane and the second plane to determine the dorsiflexion angle of the patient's foot.

19. Apparatus for determining a dorsiflexion angle of a surgical patient's foot relative to the corresponding leg during tendon surgery, said apparatus comprising:
   a leg member having a first support adapted for engaging the patent's leg adjacent at least one of a lateral malleolus and a medial malleolus of the patient, a second support opposing the first support adapted for engaging the patent's leg adjacent another of the lateral malleolus and the medial malleolus of the patient, and a reference arm extending from at least one of the first support and the second support adapted for engaging the leg of the patient at a predetermined point above the lateral malleolus and the medial malleolus of the patient; and a foot member rotatably connected to the leg member for selectively rotating the foot member relative to the leg member about an axis defined by the first support and the second support of the leg member, the foot member having a metatarsal support adapted for engaging the patent's leg adjacent a predetermined point on at least one preselected metatarsal bone of the patient.

20. Apparatus in accordance with claim 19 further comprising a gage operatively connected between the leg member and the foot member for measuring an angle between the leg member and the foot member.

21. Apparatus in accordance with claim 20 wherein the gage comprises an angle indicator connected to one of the leg member and the foot member for rotation with the respective member about the axis and a legend connected to another of the leg member and the foot member adjacent the angle indicator for indicating the angle between the leg member and the foot member, said angle being representative of the dorsiflexion angle of the surgical patient's foot.

22. Apparatus in accordance with claim 19 wherein the reference arm comprises a first end adapted to be received within an opening in one of the first support and the second support, and a second end adapted for engaging the patent's leg adjacent a head of a fibula of the patient's leg.

23. Apparatus in accordance with claim 19 wherein the reference arm comprises a first end adapted to be received within an opening in one of the first support and the second support, and a second end adapted for engaging the patent's leg adjacent a medial condyle of a tibia of the patient's leg.

24. Apparatus in accordance with claim 19 wherein the reference arm further comprises a strap attached to the reference arm for securing the reference arm to the predetermined point above the lateral malleolus and the medial malleolus of the patient.

25. Apparatus in accordance with claim 19 wherein the leg member further comprises a shin support connecting the first support to the second support and being sized and shaped for receiving a portion of the patient's shin.

26. Apparatus in accordance with claim 25 wherein the leg member further comprises a strap attached to the shin support for securing the shin support to the patient's shin to facilitate secure attachment of the leg member to the patient's leg.

27. Apparatus in accordance with claim 19 further comprising a spring for biasing the second support toward the first support to facilitate secure attachment of the leg member to the patient's leg.

28. Apparatus in accordance with claim 19 wherein the metatarsal support has a first recess for receiving a first metatarsal head of the patient's foot and a second recess opposing said first recess for receiving a fifth metatarsal head of the patient's foot.

29. Apparatus in accordance with claim 28 wherein the first and second recesses lie along a line extending obliquely with respect to the axis defined by the first support and the second support of the leg member.

30. Apparatus in accordance with claim 19 further comprising a stop connected to one of the leg member and the foot member for limiting rotation of the foot member relative to the leg member.

* * * * *